US011243661B1

(12) United States Patent
Chauvin et al.

(10) Patent No.: US 11,243,661 B1
(45) Date of Patent: Feb. 8, 2022

(54) APPARATUS, SYSTEMS, AND METHODS FOR WORKSPACE NAVIGATION IN A MEDICAL COMPUTER SYSTEM ENVIRONMENT

(71) Applicant: ALLSCRIPTS SOFTWARE, LLC, Chicago, IL (US)

(72) Inventors: George A. Chauvin, Ferrisburgh, VT (US); Jefferson Wilson, Williston, VT (US); Thomas A. Hartman, Lake Wylie, SC (US); Jeanne Marie Armstrong, Lebanon, IN (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

(21) Appl. No.: 16/265,854

(22) Filed: Feb. 1, 2019

(51) Int. Cl.
*G06F 3/0482* (2013.01)
*G16H 15/00* (2018.01)
*G06F 16/9535* (2019.01)
*G16H 10/60* (2018.01)

(52) U.S. Cl.
CPC ........ *G06F 3/0482* (2013.01); *G06F 16/9535* (2019.01); *G16H 15/00* (2018.01); *G16H 10/60* (2018.01)

(58) Field of Classification Search
CPC ........ G06F 2203/04803; G06F 3/0481; G16H 50/70
See application file for complete search history.

(56) References Cited

U.S. PATENT DOCUMENTS

| | | | |
|---|---|---|---|
| 2004/0024854 A1* | 2/2004 | Mandal | H04L 41/00 709/223 |
| 2004/0034646 A1* | 2/2004 | Kimball | G06F 16/9535 |
| 2005/0251755 A1* | 11/2005 | Mullins, II | G06F 3/0482 715/779 |
| 2005/0268306 A1* | 12/2005 | Anspach | G06F 9/451 719/313 |
| 2006/0139312 A1* | 6/2006 | Sinclair, II | G06F 3/0481 345/156 |
| 2008/0027924 A1* | 1/2008 | Hamilton | G06F 16/9535 |

(Continued)

OTHER PUBLICATIONS

J. Warren, "Cost/benefit based adaptive dialog: case study using empirical medical practice norms and intelligent split menus," Proceedings Second Australasian User Interface Conference. AUIC 2001, Gold Coast, Queensland, Australia, 2001, pp. 100-107, doi: 10.1109/AUIC.2001.906283. (Year: 2001).*

*Primary Examiner* — James T Tsai
(74) *Attorney, Agent, or Firm* — Loza & Loza, LLP; Peter Zura

(57) ABSTRACT

Technologies and techniques for providing navigation within a workspace on a processing device for electronic healthcare record systems are disclosed. Systems, apparatus, and methods disclosed provide generation of a workspace to be displayed for the processing device, which receives data relating to the workspace and at least one toolbar to be displayed with the workspace. A toolbar manager is used is process the received data related to the workspace and the at least one toolbar in order to generate at least one toolbar. The toolbar is configured according to a particular domain and includes one or more areas selectable for expanding the toolbar within the workspace to display information relevant to the particular domain.

20 Claims, 14 Drawing Sheets

(56) References Cited

U.S. PATENT DOCUMENTS

| | | | |
|---|---|---|---|
| 2008/0126982 A1* | 5/2008 | Sadikali | G06F 19/321 715/810 |
| 2013/0346907 A1* | 12/2013 | Arend | G06F 3/0481 715/779 |
| 2015/0074561 A1* | 3/2015 | Zhou | G06F 9/451 715/760 |
| 2019/0163337 A1* | 5/2019 | Gill | G06F 9/451 |
| 2020/0089664 A1* | 3/2020 | Russell | G06F 16/211 |

* cited by examiner

APPARATUS, SYSTEMS, AND METHODS FOR WORKSPACE NAVIGATION IN A MEDICAL COMPUTER SYSTEM ENVIRONMENT

FIELD OF TECHNOLOGY

The present disclosure is directed to technologies and techniques for providing workspace navigation in a medical computer system environment. More specifically, the present disclosure is directed to customizing workspaces and associated toolbars for navigation in medical computer systems.

BACKGROUND

Medical computer systems have become critical aspects of modern-day health care, and include systems such as hospital information systems (HISs), health information management (HIM) systems, electronic health record (EHR) systems and associated health information technology (HIT) that may incorporate aspects of medical record systems, medical imaging, personal health records, and patient tracking systems. These system architectures have been configured using a single level platform and/or a plurality of levels (e.g., government level, territory level, and patient carrying level) and are generally supported in client-server architectures for networking and processing.

For many of such medical record systems, applications associated with each system provide limited means for navigating workspaces within these applications. In particular, known navigation schemes do not effectively provide a combination of ways to jump to various workspaces within an application, notify the user of the system state, or support views into other workspaces while maintaining context in the main work area or workspace. Additionally, medical record systems are often not equipped to allow users to add, modify or remove information from a web resource without modifying the resource itself. Furthermore, technologies currently available do not generally allow computer systems to customize workspaces based on information provided in a web resource to suit a particular user or groups of users.

SUMMARY

Various apparatus, systems and methods are disclosed herein relating to workspace navigation in a processing device operating environment.

In some illustrative embodiments, an apparatus for providing workspace navigation on a processing device is disclosed. The apparatus includes a processor, a memory, operatively coupled to the processor, and a workspace manager. The workspace manager is configured to generate a workspace for the processing device, communications circuitry operatively coupled to the processor, wherein the communications circuitry is configured to receive data relating to the workspace and at least one toolbar. The apparatus also includes a toolbar manager configured to process the received data related to the workspace and the at least one toolbar in order to generate at least one toolbar, wherein the at least one toolbar is configured to relate to a particular domain while allowing the workspace to remain.

In other illustrative embodiments, a method for providing workspace navigation on a processing device is disclosed. The method includes generating a workspace to be displayed for the processing device and receiving data relating to the workspace and at least one toolbar to be displayed with the workspace. Further, the method includes processing via a toolbar manager the received data related to the workspace and the at least one toolbar in order to generate at least one toolbar, wherein the at least one toolbar is configured according to a particular domain and includes one or more areas selectable for expanding the toolbar within the workspace to display information relevant to the particular domain.

According to yet further illustrative embodiments, one or more non-transitory computer readable media containing computer executable instructions for performing a method to provide workspace navigation on a processing device are disclosed. The media includes code for generating a workspace to be displayed for the processing device, and code for receiving data relating to the workspace and at least one toolbar to be displayed with the workspace. Furthermore, the media includes code for processing, with a toolbar manager, the received data related to the workspace and the at least one toolbar in order to generate at least one toolbar, wherein the at least one toolbar is configured according to a particular domain and includes one or more areas selectable for expanding the toolbar within the workspace to display information relevant to the particular domain.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
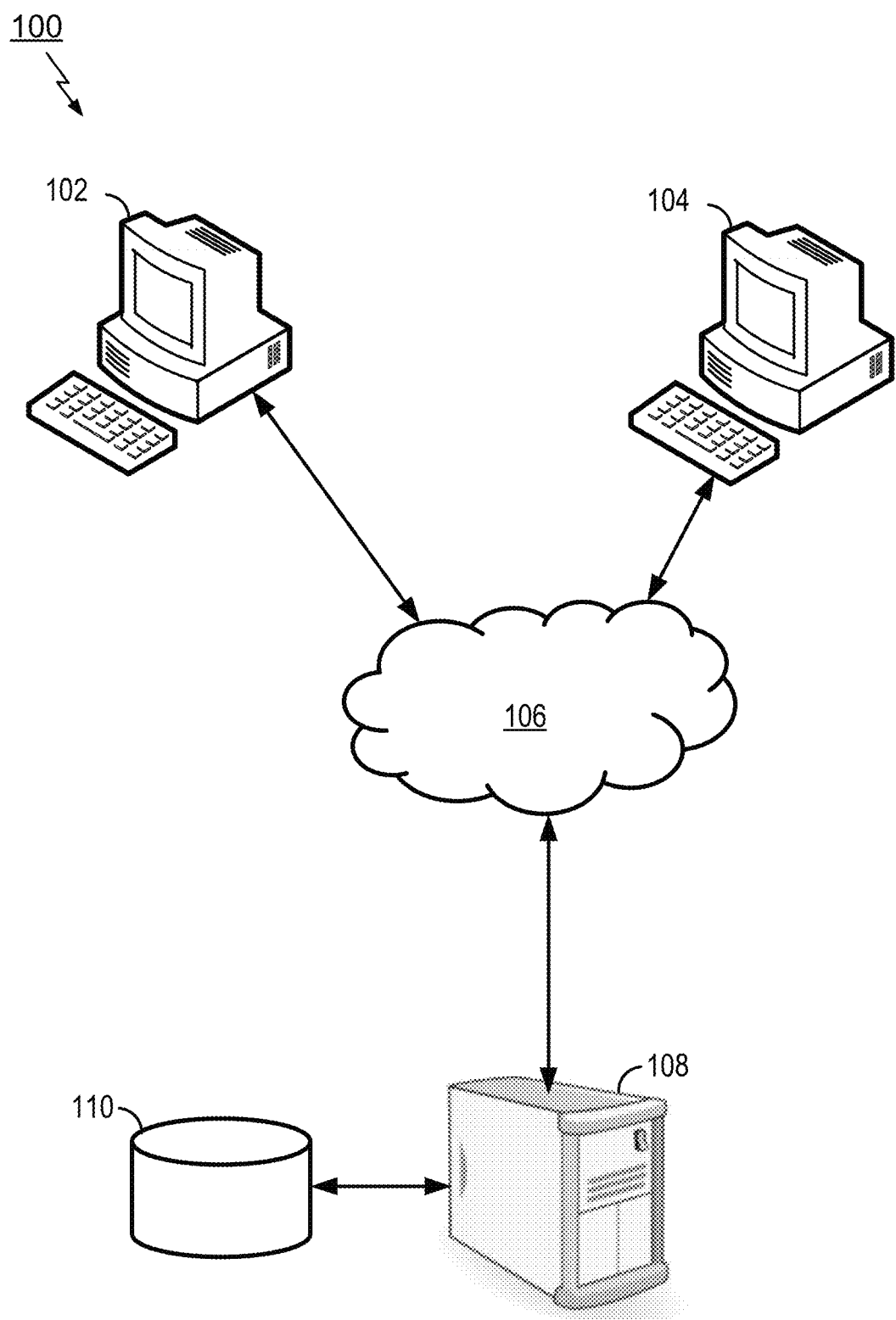
FIG. 1 illustrates a simplified view of a processor-based computer system configured to provide various workspace navigation schemes.

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that the programming techniques and hardware arrangements disclosed herein, embodied on tangible mediums, are configured to transform the conventional hardware components into new machines that operate more efficiently (e.g., providing greater and/or more robust data, while using less processing overhead and/or power consumption) and/or provide improved user workspaces and/or toolbars for human-machine interaction.

As discussed earlier, for current navigation schemes for certain medical records systems it is difficult to provide a combination of ways to jump to various workspaces within applications, notify the user of system state, and support views into other workspaces, while maintaining context in the main work area or workspace. Accordingly, the present disclosure provides navigation structures, paradigms or designs that afford better navigation, while also supporting an open architecture to allow third party development teams; e.g., to hook into the application with specific functionalities with the constraint of provided stylistic and coding standards. As will be described herein, various navigation constructs to provide better navigation may include one or more of collapsed, expanded or fly-out views allowing application-wide awareness of system occurrences, which are also configurable by domain. Further navigation constructs include a "drawer" to view and act upon cross-domain content while keeping a main content in context. Yet further navigation constructs include domain-specific notification capabilities and badging "roll-up: capabilities, and pinning/ user Personalization, interrupt handing, and main workspace resuming. Still further, the present constructs are extendible to third party applications.

Turning to FIG. 1, a system 100 is shown for generating and customizing workspaces for a computing environment in a medical records computer system. The system 100 may comprise one or more computing devices (102, 104), which may be workstations, personal computers (PCs), laptops, tablets, etc., that are coupled to a computer network 106. Server 108 may also be coupled to the network 106 and communicate with any of computing devices 102, 104. While only two computing devices are shown in the figure, those skilled in the art will recognize that any number of suitable computing devices may be coupled to network 106. Similarly, server 108 may be configured as a stand-alone server, or may be part of a server network that includes a plurality of server, or a cloud server network. Server 108 may be coupled to a central storage database 110, that stores data associated with workspaces and toolbars, including navigation paradigms for the toolbars. As will be explained in further detail below, the data from database 110, as well as data from computing devices 102 and 104 may be processed by server 108 to provide customized computer workspaces and toolbars, as well as customized navigation paradigms and schema.

Figure 2:
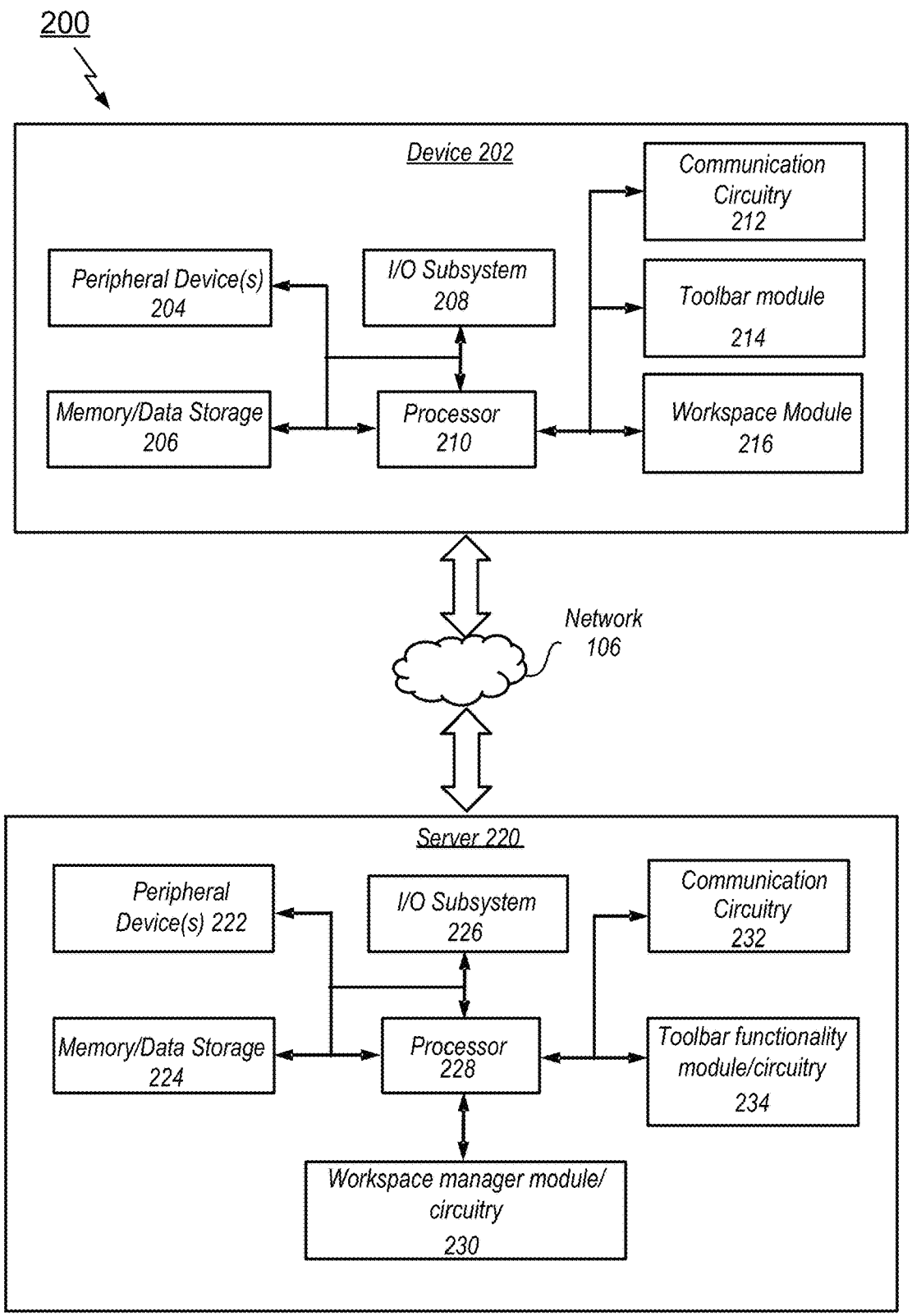
FIG. 2 schematically illustrates an operating environment for processing devices and a server communicatively coupled to a network for processing workspace and toolbar data under an illustrative embodiment.

FIG. 2 shows an operating environment for system 200 that includes a processing device 202, which may be configured as any of computer devices 102, 104, and a server 220, which may be configured as server 108, communicating via the network 106, wherein the system is configured to provide customized computer workspaces and toolbars for various different navigation constructs under an illustrative embodiment. In the illustrative embodiment, the processing device 202 includes a processor 210 or processor circuitry, one or more peripheral devices 204, memory/data storage 206, communication circuitry 212, a toolbar functionality module 214, and a workspace module 216. Toolbar functionality module 214 may be configured to operate according to known specifications.

Workspace module 216 is configured to generate workspaces for device 202 that may include, but is not limited to, toolbars, interfaces, dialog boxes, and formatting related to a medical application being executed on device 202. The workspace module 216 may be configured to receive manual input and also receive automatically generated workspace data based on data received from toolbar functionality module 214. In some illustrative embodiments, toolbar functionality module 214 and workspace module 216 may be incorporated into memory/data storage 206 with or without a secure memory area, or may be a dedicated component, or incorporated into the processor 210. Of course, processing device 202 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry and/or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any type of server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated herein for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. The server 220 also includes a toolbar manager module/circuitry 234 that is responsible for processing data from or sending data to toolbar functionality module 214 in device 202. The toolbar functionality data may be received from toolbar functionality module 214 in real-time as it is entered on device 202, or may be batch processed and/or pushed or otherwise transmitted at predetermined intervals.

Toolbar functionality data manager module 234 also communicates with workspace manager module 230. In one illustrative embodiment, toolbar functionality data manager module 234 may process the toolbar functionality data to identify if the data contains predetermined data. Additionally, toolbar functionality data manager module 234 may process the toolbar functionality data to identify similarities between the received data and one or more predetermined data. For example, the toolbar functionality data may be in the form of a JSON-LD data stream that may be additionally converted to an XML representation of the JASON-LD data for indexing purposes, and to retrieve data for either a specific object or repository-wide.

Under an illustrative embodiment, when users interact with software being executed on device 202, they may add or modify data related to a workspace, toolbar, and/or the software data itself. Once specific and/or similar toolbar data are determined, the toolbar functionality manager module 234 transmits the determined toolbar paradigm and schema to workspace manager module 230, which may be configured to modify an existing workspace and/or toolbars, and transmit the modified workspace to workspace module 216, which loads the modified workspace into device 202 during operation.

The disclosure configuration is particularly advantageous for customizing workspaces in a medical software environment, by allowing the system (e.g., 200) to customize workspaces for users. The customization may be based on any number of factors including, but not limited to, the medical position of the user (e.g., IT staff, nurse, doctor, technician, etc.), the medical process being used or reviewed during software execution (e.g., medical imaging, pharmaceutical, accounting), location of user, user team group, and so forth. As users from an organization enter customization data or selections during software use, the system (e.g., 200) may customize the workspaces to provide optimal display, positioning and functionality of the workspace to each group according to their needs and/or preferences.

In the illustrated embodiment, communication between the server 220 and the processing device 202 takes place via the network 106 that may be operatively coupled to one or more network switches (not shown). In one embodiment, the network 106 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 106 may include any number of additional devices, such as additional computers, routers, and switches, to facilitate communications between the processing device 202 and the server 220.

Figure 3:
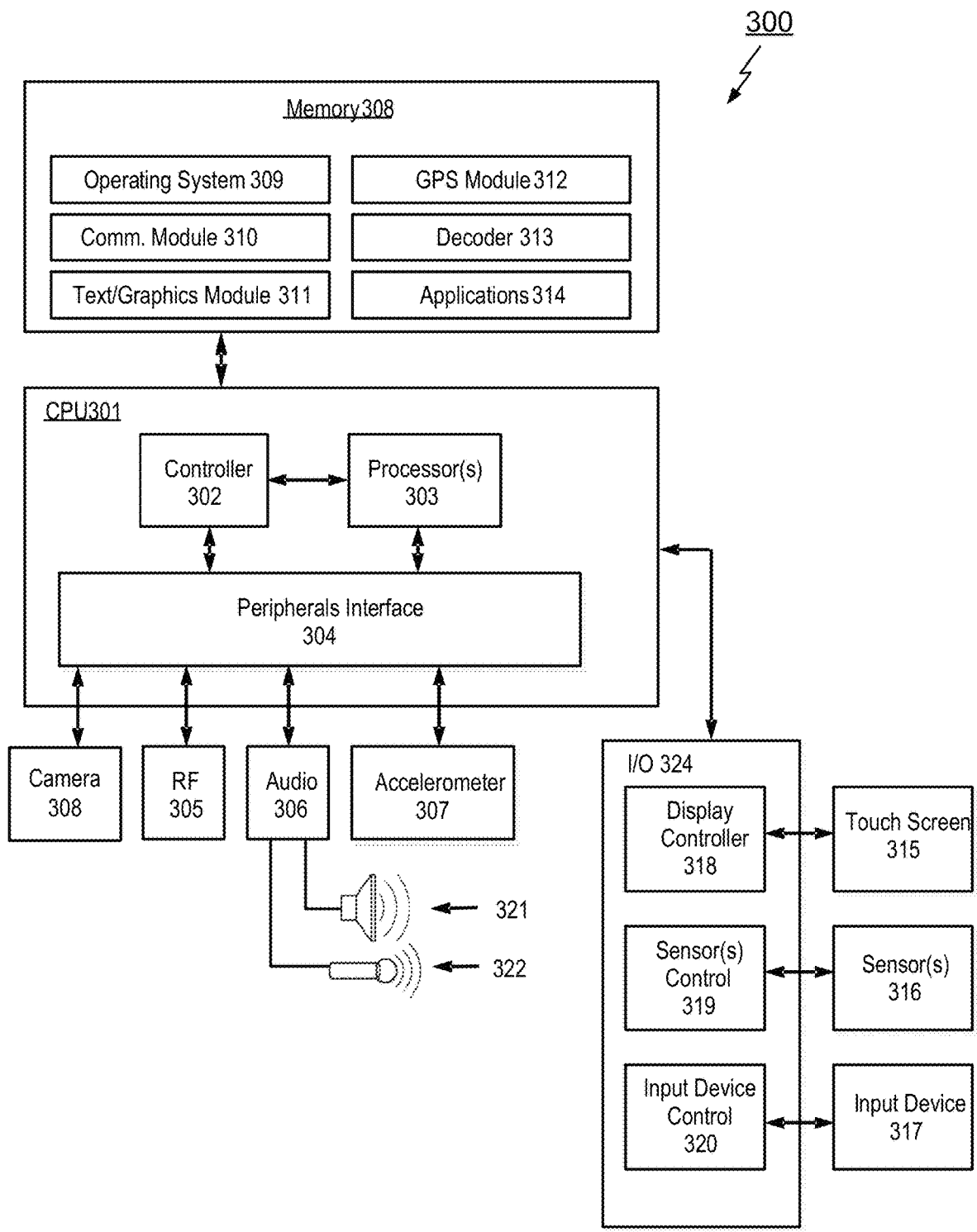
FIG. 3 schematically illustrates an operating environment for a processing device configured to process data and workspaces under an illustrative embodiment.

FIG. 3 is an exemplary embodiment of a computing device 300 (such as processing devices 102, 104, 202), and may be a personal computer, smart phone, tablet computer, laptop and the like. Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, speaker 321, microphone 322, and input/output (I/O) subsystem 324 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both ears) and input (e.g., a microphone).

I/O subsystem 324 couples input/output peripherals on the device 300, such as touch screen 315, sensors 316 and other input/control devices 317, to the peripherals interface 304. The I/O subsystem 324 may include a display controller 318, sensor controllers 319, and one or more input controllers 320 for other input or control devices. The one or more input controllers 320 receive/send electrical signals from/to other input or control devices 317. The other input/control devices 317 may include physical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/ to the touch screen 315. Touch screen 315 displays visual output to the user. The visual output may include graphics, text, icons, video, and any combination thereof. In some embodiments, some or all of the visual output may correspond to user-interface objects. Touch screen 315 has a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In an exemplary embodiment, a point of contact between a touch screen 315 and the user corresponds to a finger of the user. Touch screen 315 may use LCD (liquid crystal display) technology, or LPD (light emitting polymer display) technology, although other display technologies may be used in other embodiments. Touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 226. The accelerometer is preferably configured to output accelerometer data in the x, y, and z axes.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including health monitoring software, sensor software, navigation software, mapping, address books/contact list, email, instant messaging, and the like.

Figure 4:
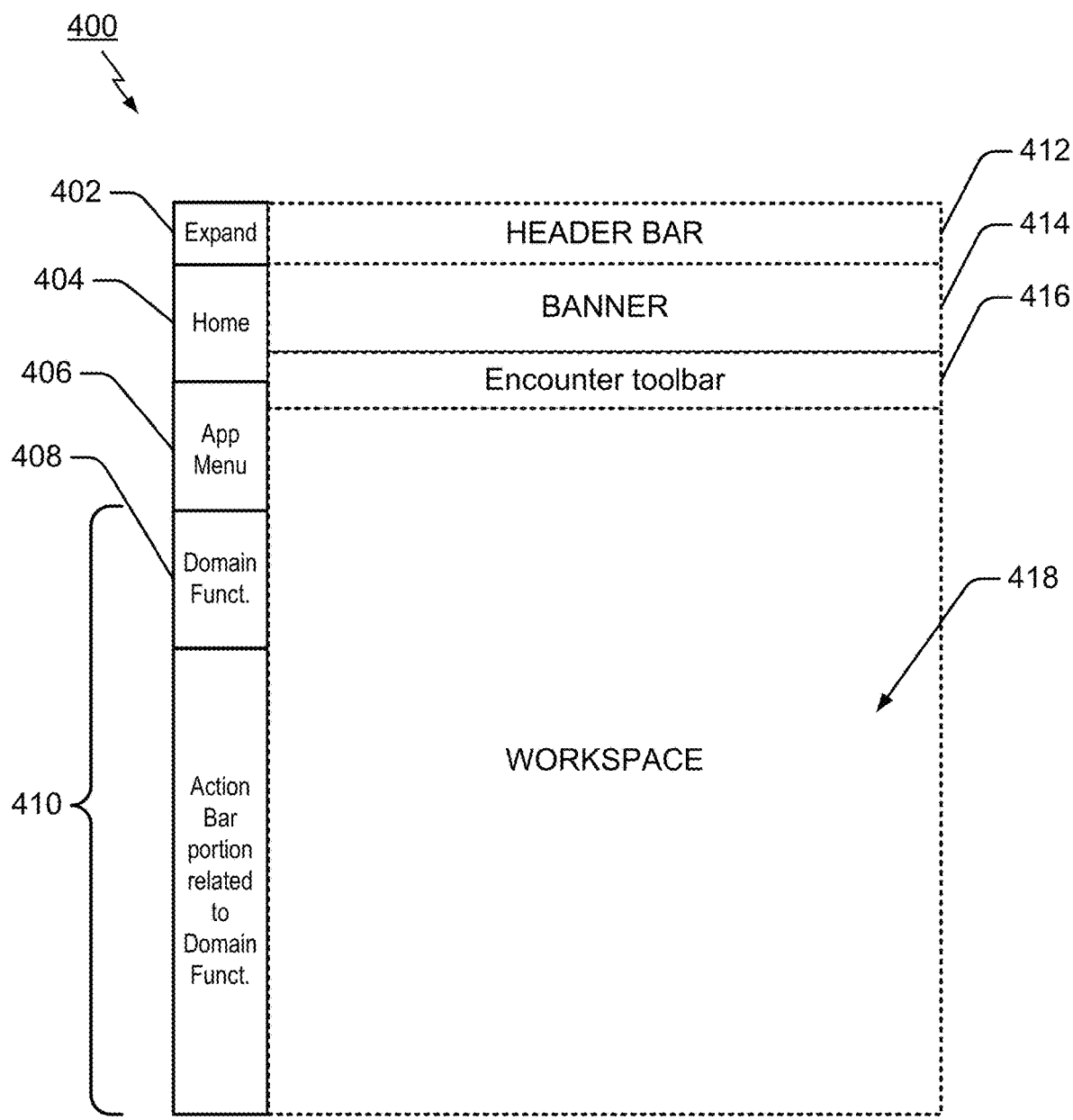
FIG. 4 shows a toolbar configuration for a workspace under an illustrative embodiment.

Turning to FIG. 4, an exemplary display configuration is illustrated that includes a toolbar or taskbar 400 configuration to provide navigation of an application functions within a workspace. In some illustrative embodiments, the toolbar 400 may be configured to have a plurality of portions, elements, or fields 402-410, wherein each portion 402-410 is associated with different functionalities. In the example of FIG. 4, the toolbar 400 may have a view toggle or toolbar expand area 402, a home area 404, an application menu area 406, and an toolbar area termed herein as an "action bar" area 410 that may be related to the domain specific functionality and include action elements. When minimized the action bar area 410 may be displayed as a minimized domain or workspace specific functionality area 408.

The view area 402 may be configured to allow a user to access always-accessible components that afford quick access or navigation to key application functions and to increase or expand the toolbar 400. Additionally, as the view of the toolbar 400 is expanded, this brings into view various elements. In the example of FIG. 4, exemplary elements are shown by header 412, a banner 414 for customization, a further toolbar 416 that may be related to a selected domain function as will be described later, and a workspace 418.

It is noted that the action bar area 410 is configured such that the associated domain or workspace functionality is a customizable domain functionality. As will be illustrated herein, in one example this area 410 (and area 408 in the minimized state) may constitute a patient domain functionality in the context of health records system applications, but the principles disclosed herein are to be understood as being applicable to other applications and software. According to further aspects, the action bar area 410 related to the domain functionality includes various customizable action elements, which are always-accessible elements that allow quick access to various key application functions. In particular, the action bar area 410 may be configured to serve as a jump point for application navigation and system indicators. In yet further aspects, the action bar area 410 may be configured to be extensible, such that the action bar may support further third party integration. Of course, those skilled in the art will recognize that the embodiment of FIG. 4 is merely one example, and that a plurality of different configurations is contemplated in the present disclosure.

As will be described below, the presently disclosed action bar functionality of area 410 is designed to provide visibility for a user into application-wide information and system states. Specifically, the action elements therein may provide various actions such as launching a specific page in the workspace 418, expanding the action bar 410 to open a specific content area, providing a hover over functionality (e.g., expansion when a cursor is placed in the area but no mouse click or touch selection has yet been taken) to afford fly-out, fly-out drawer, or tip areas.

Figure 5:
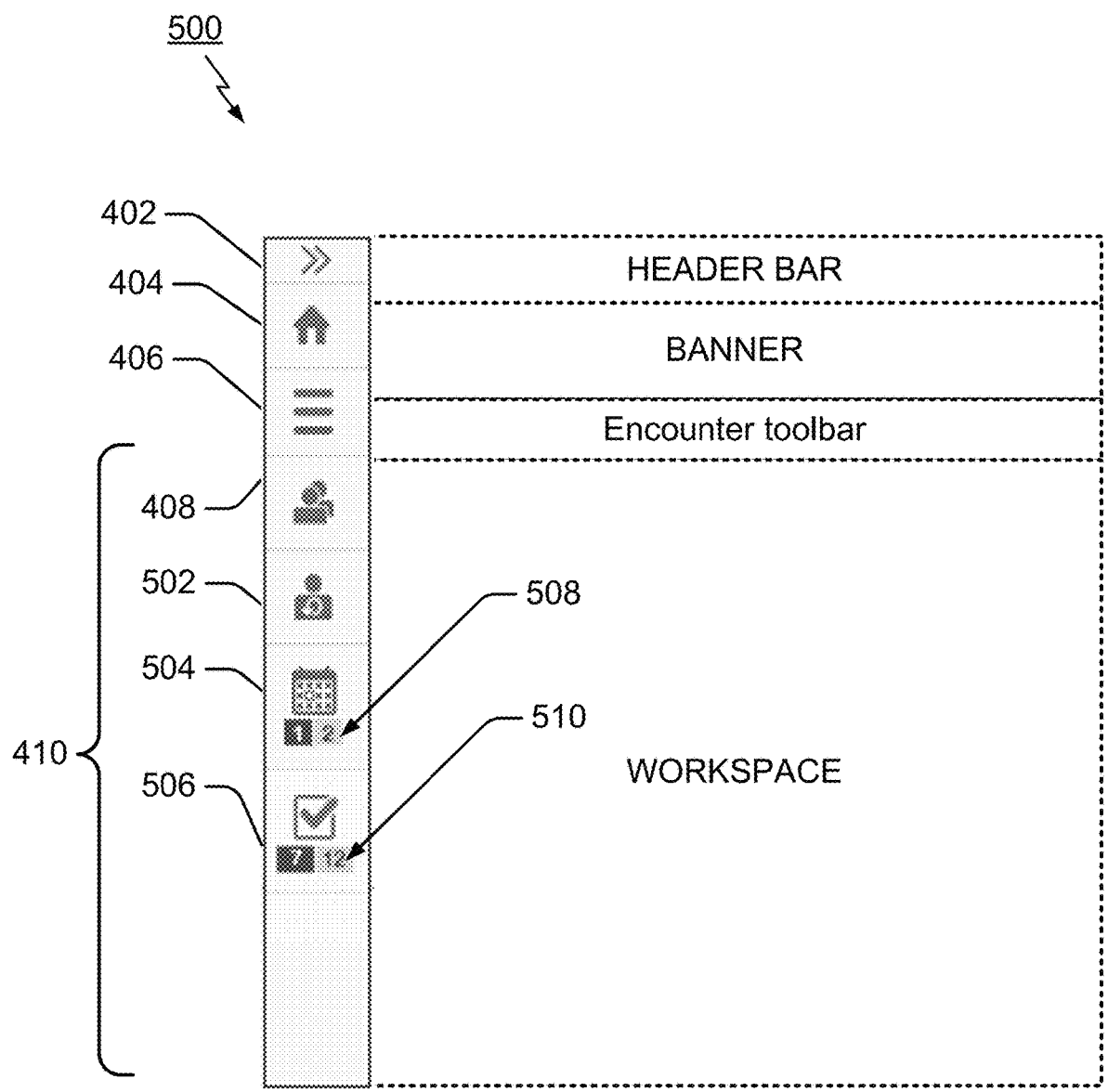
FIG. 5 shows an exemplary toolbar configuration for a processing device including action bar items for selecting action items under an illustrative embodiment.

FIG. 5 illustrates an exemplary configuration 500 for the toolbar of FIG. 4 including action bar elements or items for selecting actions under an illustrative embodiment. The illustrated toolbar configuration 500 includes areas 402-410 as discussed with respect to FIG. 4, but with examples of particular icons/symbols shown. The action bar area 410 is further detailed to illustrate examples of action items 502, 504, and 506 that may be implemented. In this case, a patient file refresh 502, a schedule/calendar/appointment action with numerical badge indications or notifications of urgent items in area 504, and task actions also with numerical badge indications or notifications of urgent task items in area 506, which will be described in further detail later with respect to FIG. 8.

The action bar areas (e.g., 502, 504, and 506) are configured to support hover interactions (or other non-hard selection interactions), wherein the interaction serves to expose fly-out content areas (i.e., a temporally displayed content area that remain in view as long as a cursor is hovered over a particular area or some other means such as touch screens with means of hovering without selection). In an aspect, the content areas that fly-out may be displayed over main application regions.

Figure 6:
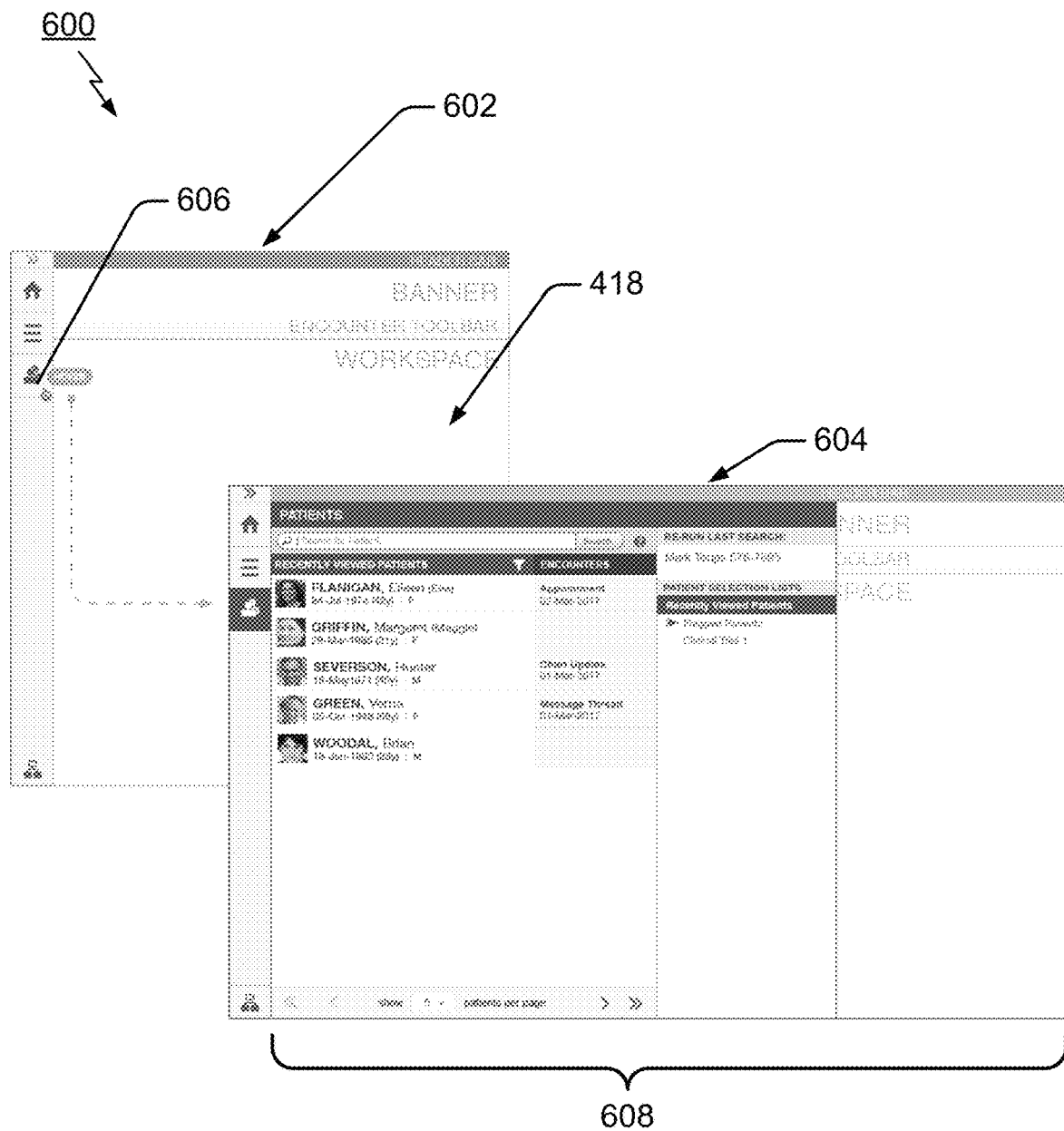
FIG. 6 shows a more detailed workspace toolbar configuration under an illustrative embodiment.

As an example of fly-out areas according to the present system, FIG. 6 illustrates an example of fly-out displays 600 that may be implemented in the present system. The illustration shows temporal changes of before cursor hovering at 602 and after cursor hovering at 604. In the particular illustrated example, when a cursor is hovered over the action bar area 606 (e.g., domain function 408 illustrated in FIG. 4) concerning patients, the fly-out area 608 will appear over the workspace 418 to show the domain specific information, which in this case is patient information, but this is merely exemplary and the domain functionality is not limited to such. The fly-out area 608 will persist until the user either takes an action within the fly-out area (which may then also serve to close the area) or moves the cursor outside of the fly-out area, which results in the area being closed or not displayed any longer. Again, the content of the fly-out areas such as 608 will be dependent on a specific domain and is not limited to merely the illustrated example of patient information. It is noted that fly-out areas such as 608 may afford efficiencies in a clinical environment, where alert-fatigue and interruption recovery are known issues. The use of the fly-out allows clinical users to maintain a consistent workspace underneath the fly-out, while gathering clinical information presented by the fly-out thereby allowing the user to make better clinical decisions.

Figure 7:
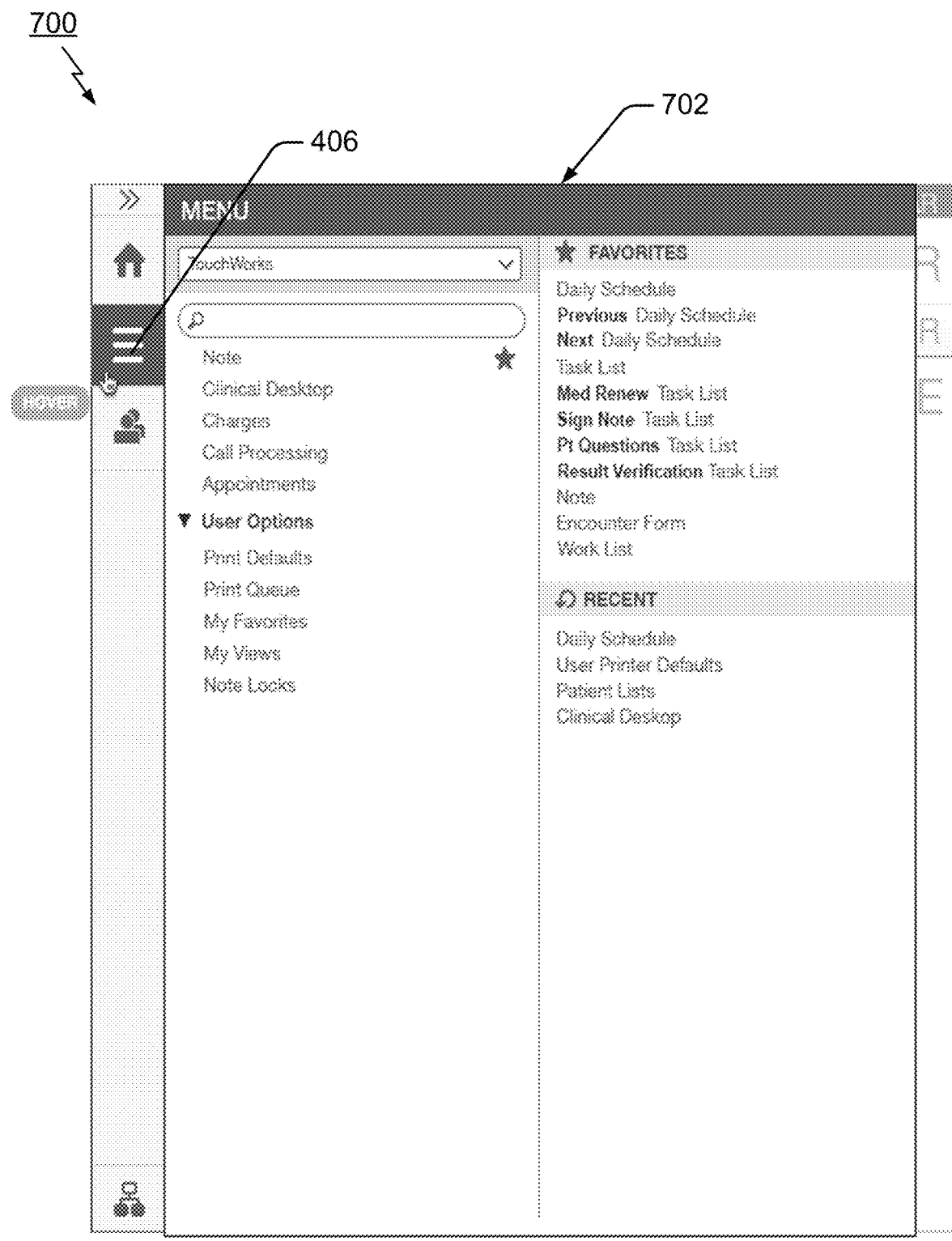
FIG. 7 illustrates another example of a fly-out area resultant from cursor hovering under an illustrative embodiment.

FIG. 7 illustrates another example 700 of a fly-out area resultant from cursor hovering over another area of the presently disclosed toolbar. In this particular example in FIG. 7, when a cursor is hovered over the index menu area 406, the resultant fly-out 702 is the menu showing all various functions of the domain. Again, this representation is merely exemplary and displays of other information types are contemplated as well.

It is noted that according to some implementations, not all of the action element areas in the toolbar will need to support fly-outs. For example, the home page action element 404 would not need to have a fly-out). In such cases, the hover interaction might simply expose a tool tip, for example. Additionally, the fly-out behaviors for the various areas of the toolbar may be customizable and determined by the party responsible for the domain including a third party integration developer. It is further noted that fly-outs could be invoked not only by cursor hover interaction, but also with touch screen functionalities or with keyboard shortcuts, as examples.

Turning back to FIG. 5, it is noted that action elements (e.g., 504 or 506) in the action bar (e.g., 410) are configurable to support notification icons or "badges", examples of which may be seen in area 504 (e.g., calendar element) at 508 or in area 506 (e.g., task checkmark/list) at 510. These notification badges can be configured by domain, as well as by third party development teams for integration. According to an aspect, the notification badges may further be configured to be refreshed asynchronously (i.e., no full page refresh is required) to give real-time indication of system-state.

Figure 8:
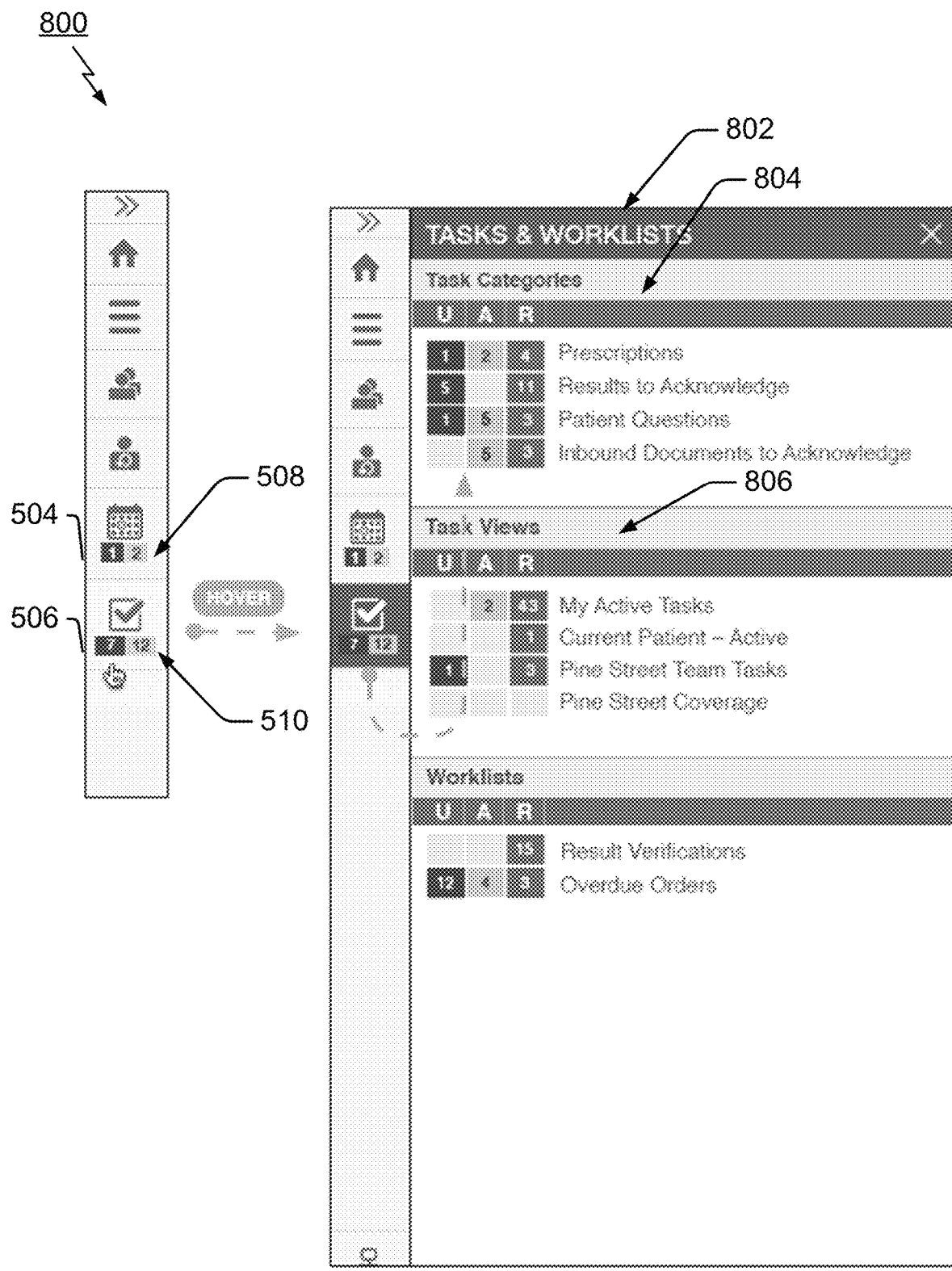
FIG. 8 shows an exemplary implementation of badge notifications and their functionalities under an illustrative embodiment.

As an example of the badge notifications, FIG. 8 shows an exemplary implementation of badge notifications and their functionalities. In this example, the badges 508 or 510 can be configured to define "Urgent" (e.g., left hand portion of the badge) and "High" (right hand portion of the badge) status action items and also display the numbers thereof (i.e., 7 and 12, respectively in the example) to be driven by the specific functionality particular to the domain. In the example of FIG. 8, the badge notifications for the schedule icon (i.e., area 504) are updated when there are patients waiting past a defined time threshold and the tasking icon (i.e., area 506) display levels of urgency for specific task types, such as through different color schemes (e.g., red for most urgent and yellow for high urgency). In other aspects, the notification badges can also be designed to have a neutral state. In this example, the action bar notification badges in taking area 506 display counts or sums of the most urgent and urgent tasks making up the task category buckets. Also in this example, it is noted that the "Routine" items do not contribute to the counts shown in the notification badges, but the disclosure is not limited to such preclusion, and the notifications are instead configurable per domain.

In the example of FIG. 8, the action elements 504 or 506 may be configured such that when a cursor hovers over these areas, a fly-out or expanded area 802 is displayed where the displayed area 802 in FIG. 8 relates specifically to the tasking icon (area 506). Thus, in the illustrated example, when a cursor hovers over that task list area or icon 506, a task and worklist fly-out may be displayed showing various task categories 804 including the most urgent categories under the letter "U", high urgency categories under the letter "A" and neutral or routine task categories under the letter "R". This enables a user to quickly navigate to see those task categories under the badge notifications (e.g., 7 most urgent task categories and 12 high urgency task categories). For action elements that support notification badges (e.g., areas 504 or 506 in the examples of FIGS. 5 and 8), the detailed views (i.e., fly-out or expanded view as shown at 802 in FIG. 8) support the ability to break out the individual elements that contribute to the total count shown in the areas 504 or 506 of the action bar.

Figure 9:
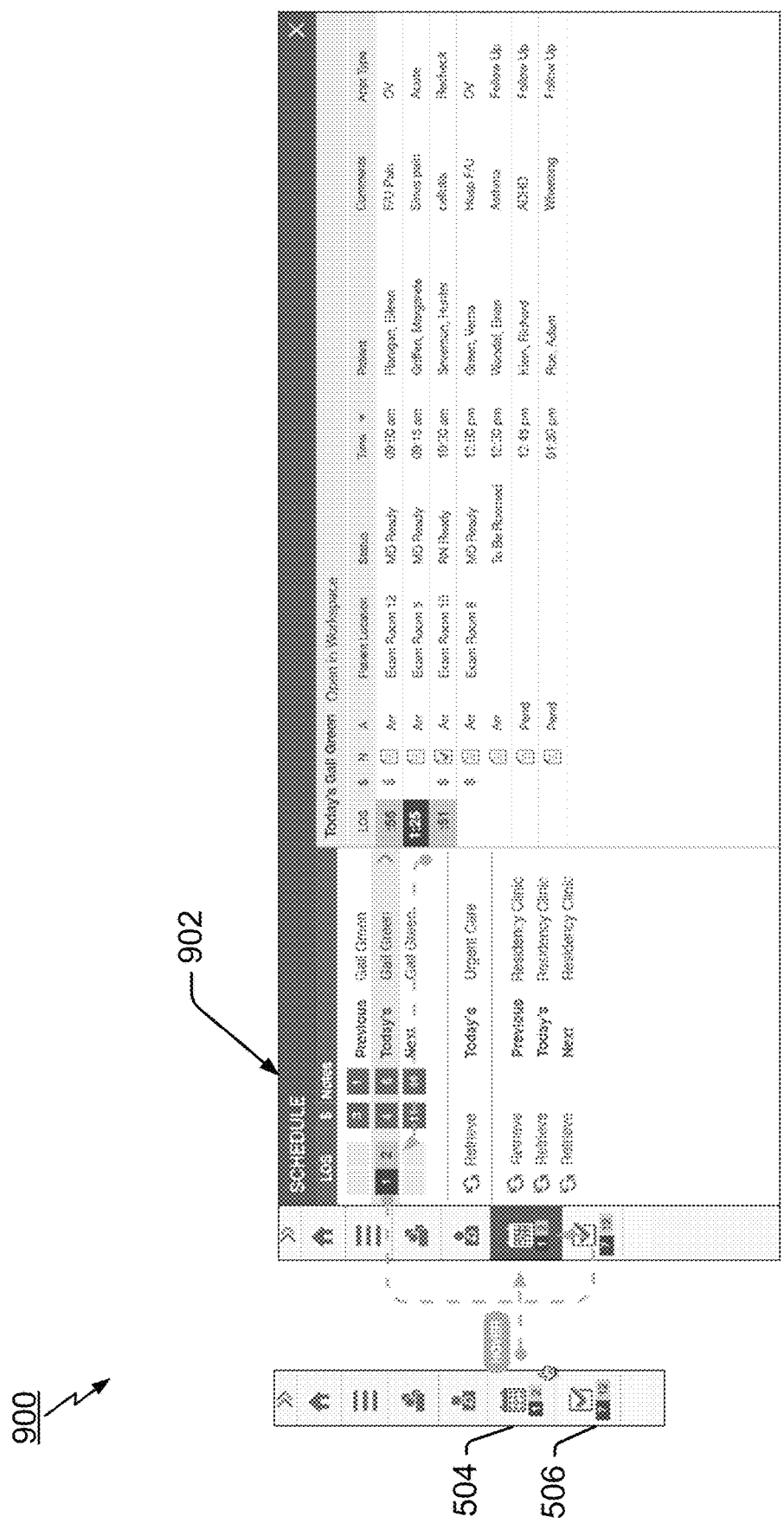
FIG. 9 illustrates another exemplary implementation of badge notifications and their functionalities under an illustrative embodiment.

FIG. 9 illustrates another exemplary implementation of badge notifications and their functionalities. In this example, the action bar notification badges in the scheduling area or module 504 may be configured to display of count or sum of time-thresholds. When a cursor is hovered over the area 504, a fly-out display 902 may be displayed that shows a schedule, such as the schedule for a healthcare provider user. In other embodiments the badges may be color coded such as red meaning that the schedule items has been pending for greater than 60 minutes and yellow meaning that the schedule items has been pending for greater than 30 minutes.

Figure 10:
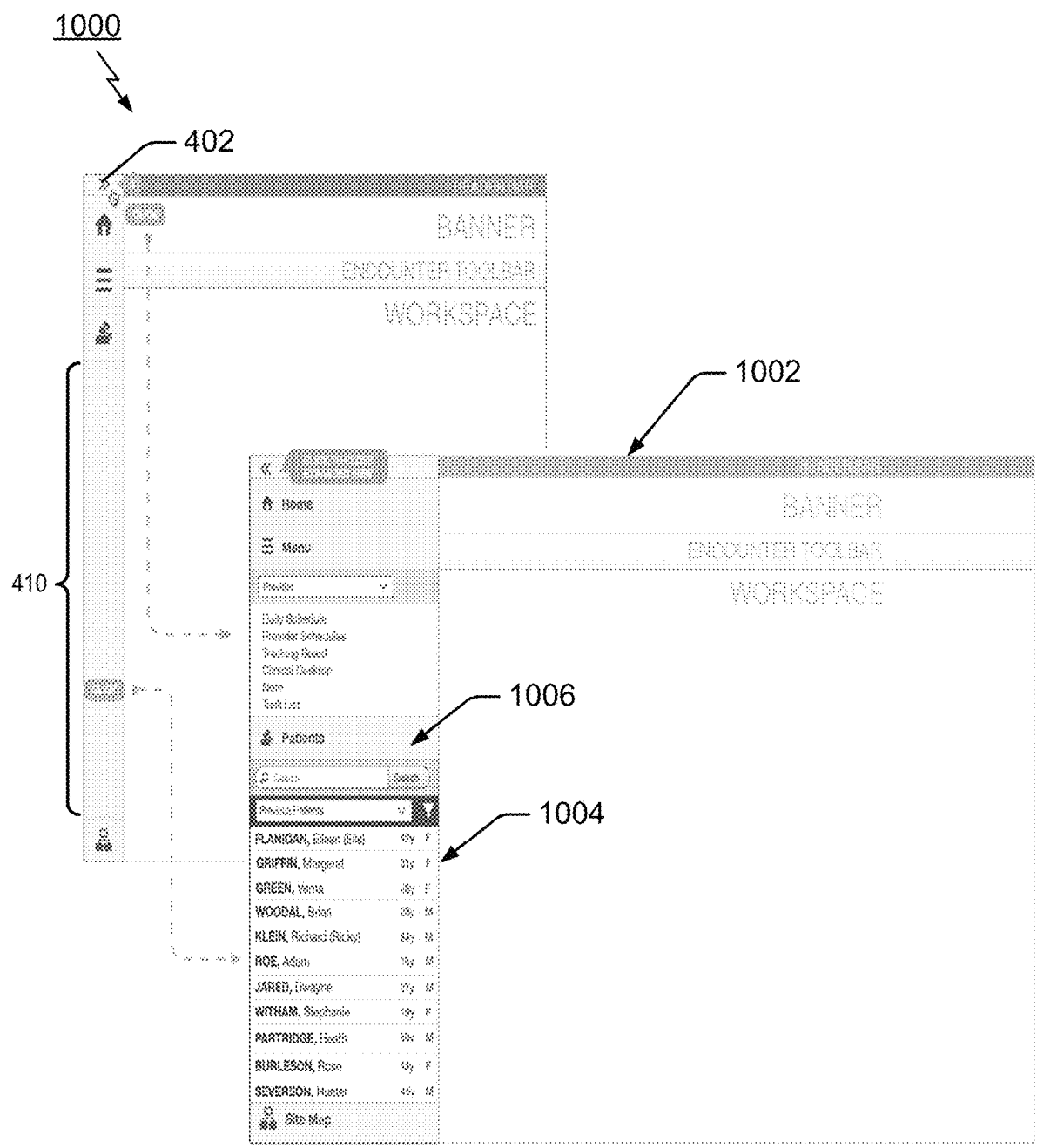
FIG. 10 illustrates a further feature of the disclosed toolbar of providing interactive capabilities of the expanded view.

FIG. 10 illustrates further features of the disclosed toolbar wherein interactive capabilities of the expanded view are provided as shown generally at 1000. In this example, the action toolbar (e.g., 410) is configured to support an expanded view 1002 that affords a user the ability to keep an expanded area of the toolbar open until an action is taken to close it. The expanded view may be accessed by clicking or touching the expand area icon 402 at the top of the toolbar, and then clicking or touching anywhere on the action toolbar 410 that does not have an action element. In other aspects, a shortcut key(s) on a keyboard may be assigned to cause expansion as well. Additionally, the area shown at reference number 1004 may be extended by a user either vertically or horizontally, such as by dragging from the top, bottom, or side edges of the area 1004. Further, the display may be configured such that a user may click on a header (e.g., 1006) in an action element area to provide more vertical space or area for a particular desired section.

According to other certain aspects, the system may be configured to remember or store data or metadata concerning the state of the action toolbar as illustrated by FIG. 10 per each user across multiple sessions for user personalization and convenience. Such information or data stored may include whether the state was expanded or collapsed, what the particular width of the fly-out display was if the toolbar was expanded, and/or what action element or area was last visible in the expanded view. The action toolbar may also be configured to support a pinning mechanism that allows the action toolbar's expanded state to cover the workspace area until pinned by the user. Accordingly, being an unpinned state, the fly-out would only persist while the cursor is over the workspace area, for example.

Figure 11:
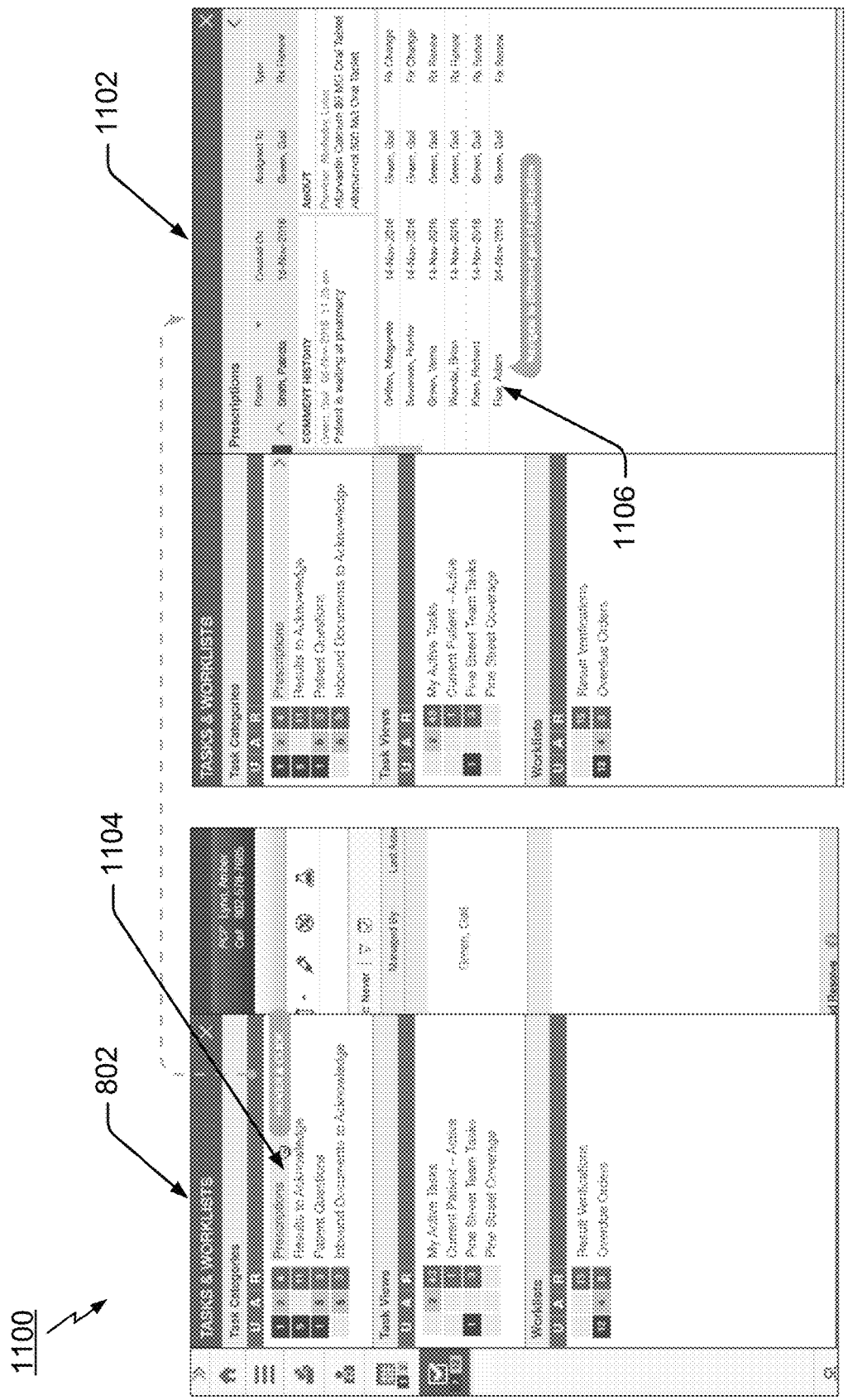
FIG. 11 illustrates an exemplary embodiment having further navigation features including an action toolbar area supporting an additional expansion providing a detailed view of a specific domain.

FIG. 11 illustrates an example 1100 having further navigation features including the action toolbar area or navigation panel supporting an additional expansion or "navigation drawer" that provides a detailed view of a specific domain. Here the action toolbar navigation panel 802, which was previously illustrated in FIG. 8, supports the expansion of an additional drawer 1102 affording a further detailed view of the specific domain as may be seen in the illustration on the right hand side of FIG. 11, which shows expansion after a user action (i.e., hover and/or click/touch). In particular, when a user clicks or screen touches a particular area 1104 (e.g., a prescriptions category as illustrated in the example of FIG. 11), the navigation drawer 1102 is displayed. In an aspect the drawer area 1102 is displayed over the main workspace area, which allows a user to keep the current context of the workspace while viewing the specifics of the other domain exposed via the fly-out view (e.g., 802). Yet further, it is noted that a user can decide to jump or navigate to another part of the application from the drawer mechanism workspace 1102, or return back to the workspace in the context shown prior to the opening of drawer mechanism workspace 1102. As an example of the former option, a user may click on a patient name as shown at reference 1106 to navigate to patient history information.

Figure 12:
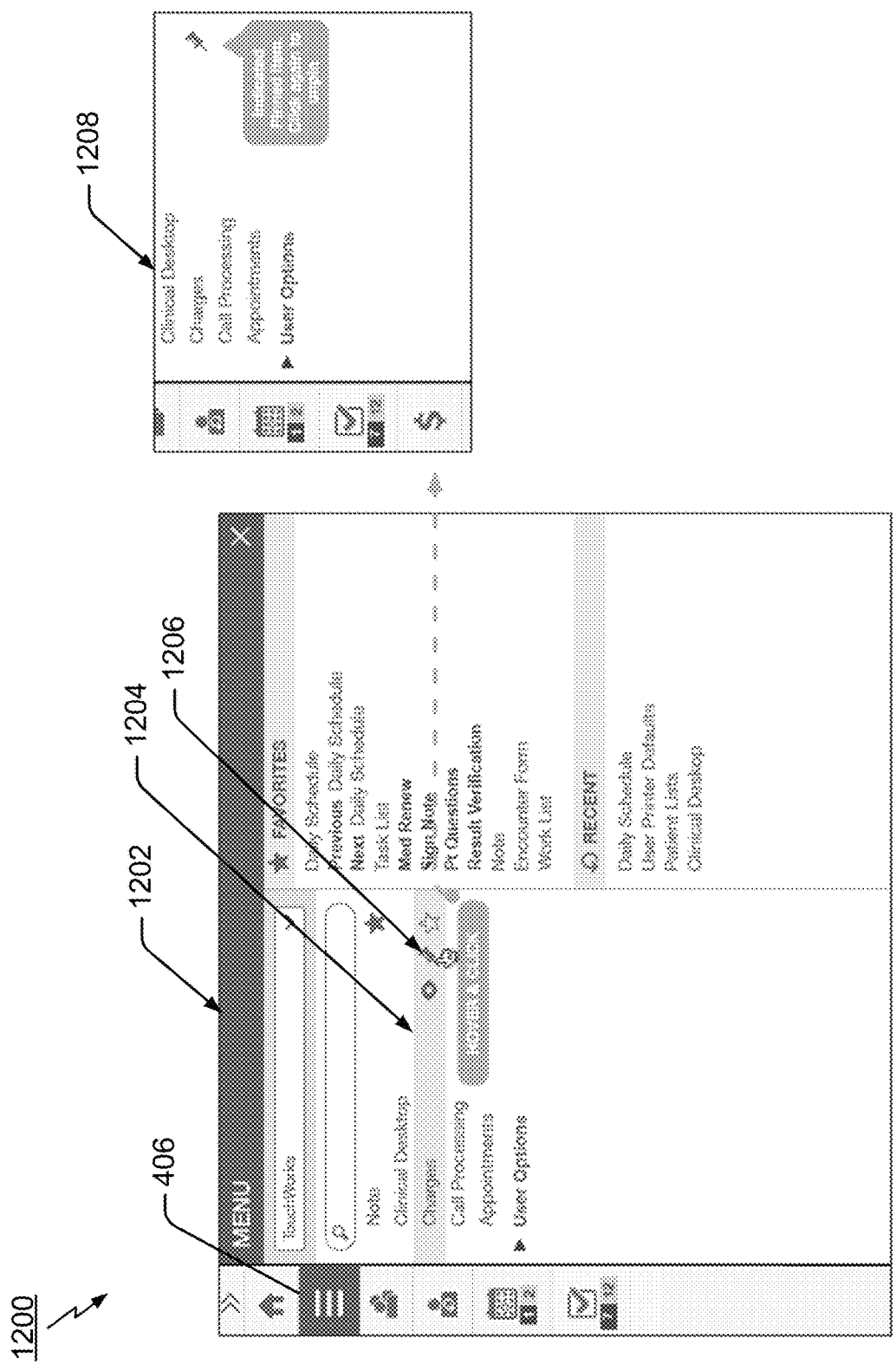
FIG. 12 illustrates yet another aspect of the present navigation scheme wherein the action toolbar supports further one-click navigation.

FIG. 12 illustrates yet another aspect of the present navigation scheme wherein the action toolbar supports further one-click navigation. As shown in FIG. 12, when the menu area 406 is selected, the resulting fly-out area 1202 will include various selections or navigational item wherein a pin icon or area is viewable when the cursor is hovered over each selection. In the illustrated example, when a cursor is hovered over the "Charges" selection 1204, a pin icon or area 1206 is available. When a user clicks or touches this pin icon 1206, this promotes the specific navigational item from the menu to a collapsed action toolbar (not shown) to enable a one-click navigational item to go directly to a specific workspace.

Of further note, the disclosed navigation scheme may be configured to support integration extension to allow third parties to place navigation and notification elements in the action toolbar area (e.g., area 410 shown in FIG. 4). In an example embodiment, the present system allows for third party navigation or notification elements that also provide enhanced navigation to workspace pages, as well as the ability to see information and system-state notifications within the action elements and the fly-outs without navigation away from the workspace in context.

Under the examples provided herein, access to custom functionalities via the disclosed toolbars may be specific to corresponding workspace domains as discussed above. Additionally, the toolbar may be implemented by the workspace module/circuitry 216 or toolbar functionality modules/circuitry 214 or 234, or a combination thereof. After an initial setup, the workspace manager module 214 or 234 may be configured to make subsequent modifications to the workspace and/or toolbars. In this example, page administration may be utilized via a workspace type(s) and page context options may be provided via dialog type(s). Once configured the system (e.g., 200) displays the configured workspace and associated toolbar(s) during operation of the software as illustrated in FIG. 4.

Figure 13:
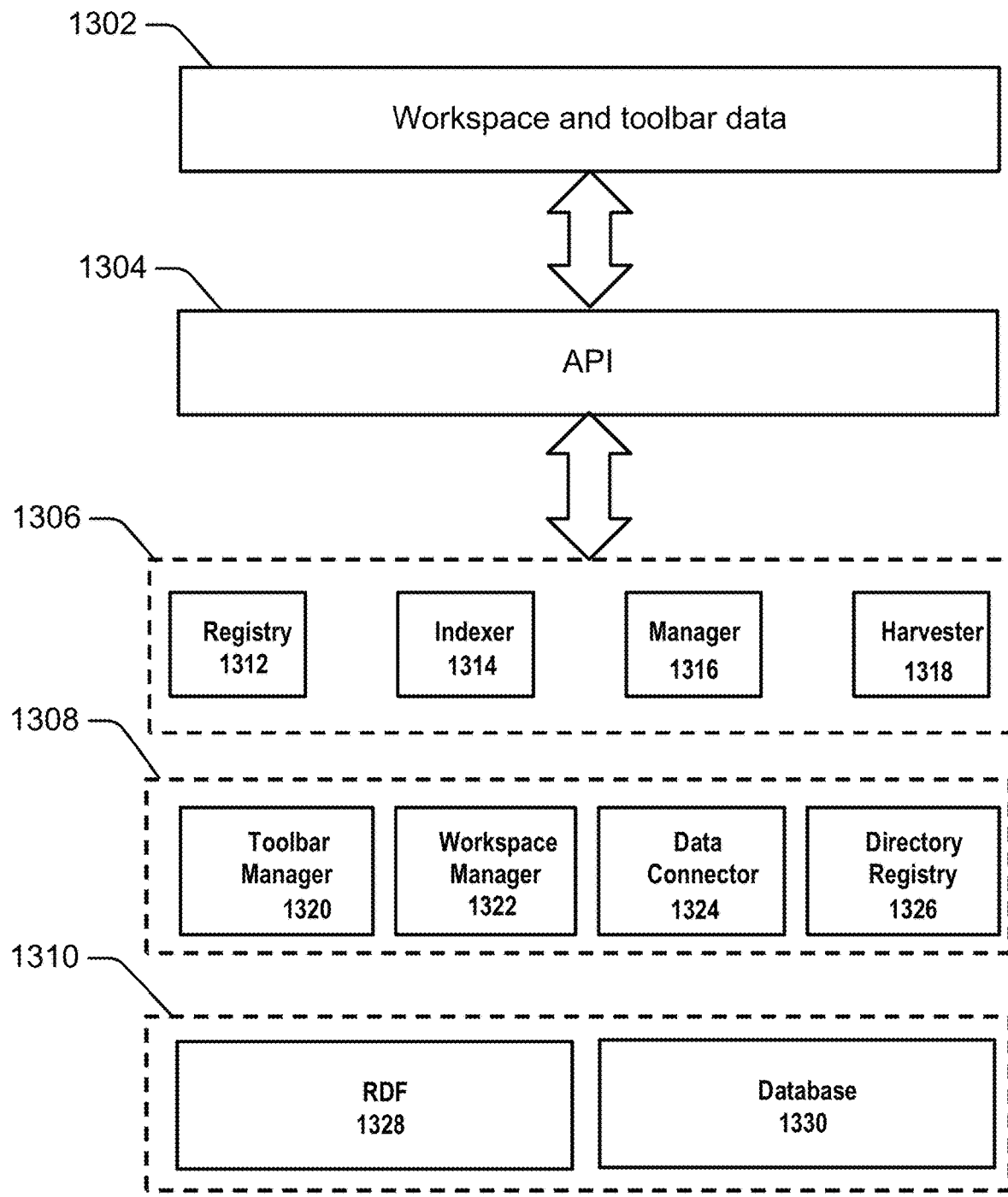
FIG. 13 illustrates an exemplary operating environment for a toolbar functionality manager module under an illustrative embodiment.

Turning to FIG. 13, an exemplary operating environment 1300 is shown for a toolbar functionality manager module (e.g., 234) under an illustrative embodiment. In some illustrative embodiments, the toolbar functionality manager module may include an application programming interface (API) 1304 that receives workspace and toolbar data and associated metadata 1302 as shown in the figure. The operating environment 1300 may be further configured to include a core layer 1306, an extension layer 1308 and a storage layer 1310 operatively or communicatively coupled to the API 1304.

Core layer 1306 may include a registry module 1312, an indexer module 1314, a metadata manager module 1316 and a harvester module 1318. Registry module 1312 may be configured to support systematic handling of heterogeneous metadata schemas, and may be based on a key-value data model for storing, retrieving, and managing associative arrays, and dictionary or hash table data structures. Dictionaries contain a collection of objects, or records associated with annotations, which in turn have many different fields within them, each containing data. These records are stored and retrieved using a key that uniquely identifies the record, and is used to quickly find the data within the database. Registry module 1312 may be configured to register either a single metadata schema that exclusively describes administrative, descriptive, structural metadata or a community-defined METS XML that may comprise multiple metadata schemas. The registry module 1312 allows managers of a medical software system to maintain multiple metadata schemas with different versions. In the case of a single metadata schema, the schema may be registered as a key-value pair, where a key may be the combination of schema namespace and version and the value is the complete schema. In the case of a METS XML, the metadata schemas used in constructing the various sections of the METS profile are extracted and individually registered. A relation map of the metadata schemas and the corresponding METS-profile may also be created. This relation map may be used to segregate incoming metadata and for reconstructing the metadata during the harvesting stage.

For enabling full-text search over metadata an indexer module 1314 may be linked to the registry module 1312, where the indexer module 1314 executes a depth-first search, or other suitable search algorithm to recursively iterate the XSD or XML, and during each iteration, add a unique index term path the list. Metadata manager 1316 may be configured to analyze the metadata associated with annotations to determine a corresponding schema and version from the key-value store. Based on the corresponding version of the available schema, metadata manager 1316 may perform a schema conformance check and convert the validated metadata into a suitable format (e.g. JavaScript Object Notation (JSON) Data Interchange Format) for data storage. Harvester module 1318 may be based on Open Archives Initiative Protocol for Metadata Harvesting (OAI-PMH), or other suitable platform for harvesting or collecting metadata.

Extension layer 1308 may be configured to integrate various third-party tools and technologies with the core layer 1306 and may support reuse of existing tools, software libraries, web-services, or databases. Extension 1308 layer may include a toolbar manager module 1320 that may be configured to configure toolbars, such as the action toolbar disclosed herein, with the received data or with user input customization data as they evolve during use. Workspace manager module 1322 is configured to generate and maintain the workspace, such as a workspace for an API. Data connector module 1324 may be configured to support annotation and metadata indexing and search functions. In some illustrative embodiments, data connector module 1324 may map schemas an annotation collections or create indexes with multiple types corresponding to different embedded schemas. Directory registry module 1326 integrates and manages the various annotations, metadata and schemas into directories for access and searching.

Storage layer 1310 may include a Resource Description Framework (RDF) store 1328 (or "triplestore") to function as a graph database for storing annotations and metadata as semantic facts. The database may function to allow storage and retrieval of triples through semantic queries. Typically, a triple will be configured as a data entity composed as a subject-predicate-object (e.g., "x-ray needs icon", "Bob is hypoglycemic", "screen is small", etc.). In some illustrative embodiments, RDF store 1328 may be configured to infer implicit facts out of the explicit statements of annotations and/or associated metadata. Inferencing relationships out of the original data may be accomplished using, for example, a semantic graph database (e.g. GraphDB), turns information into knowledge. In some illustrative embodiments, the RDF store 1328 may also facilitate many text analytics techniques such as extracting information from unstructured data and enriching content. By 'learning' the meaning as well as the context in which entities are used, machine learning algorithms can be used to classify entities and disambiguate between them. Apart from defining relationships, RDF triples also allow links between databases with structured data and documents that contain unstructured, free-flowing text. In this way, RDF triplestores connect entities from databases to documents that mention these entities.

Storage layer 1310 may also include database 1330 that may be configured as one or more databases. In one illustrative embodiment, database 1330 may be configured as a multi-model database (e.g., ArangoDB) that supports a plurality of data models, such as key/value, documents and graphs, utilizing one database core and a unified query language. IN some illustrative embodiments, the query language may be declarative and allow combinations of different data access patterns in a single query. In one example, the database 1330 may be configured as a NoSQL database.

Using the configuration of FIG. 13, users of the system (e.g., 200) may load and execute workspaces and/or toolbars configured under a first set of operational layouts and/or parameters. During the course of usage, users may access aspects of the workspace, including dialog boxes, toolbars, icons and the like on their processing device (e.g., 202). At a predetermined time (e.g., expiration of time period, closing of the workspace, etc.) the workspace/toolbar data and associated metadata are transmitted to the server (e.g., 220) for processing. Typically, associated metadata may include, but is not limited to, the processing device ID, user information (e.g., department, user position/department, location, user age, etc.) medical context (e.g., patient, treatment, medical condition. etc.) and other data. When the data and metadata are received in the server, they are processed via operating environment 1300 to extract all workspace/toolbar data and metadata. The extracted data and metadata are then processed in operating environment 1300.

The workspace manager module 230 may be used to modify the existing workspace according to the customization provided by or selected by the user, and save the modified workspace with an identification particular to the navigational schema. The modifications may include changes to the workspace including, but not limited to, addition or deletion of toolbar icons and/or functions, placement of toolbars and/or functions, dialog box placement or content, order of data presentation, level of interaction with workspace items or icons (e.g., single click vs. double-click), hover actions, fly-out configurations, drawer configurations, presentation of data on the workspace, and so forth. In some illustrative embodiments, the modifications to the workspace may be particular to an individual user. In some illustrative embodiments, the workspace manager module 230 may normalize data received from a plurality of users and provide a normalized workspace as part of the modification process. In some illustrative embodiments, the modifications may be conditioned on associated metadata, where only data containing authorized metadata may be authorized and used for modifying the workspace.

Figure 14:
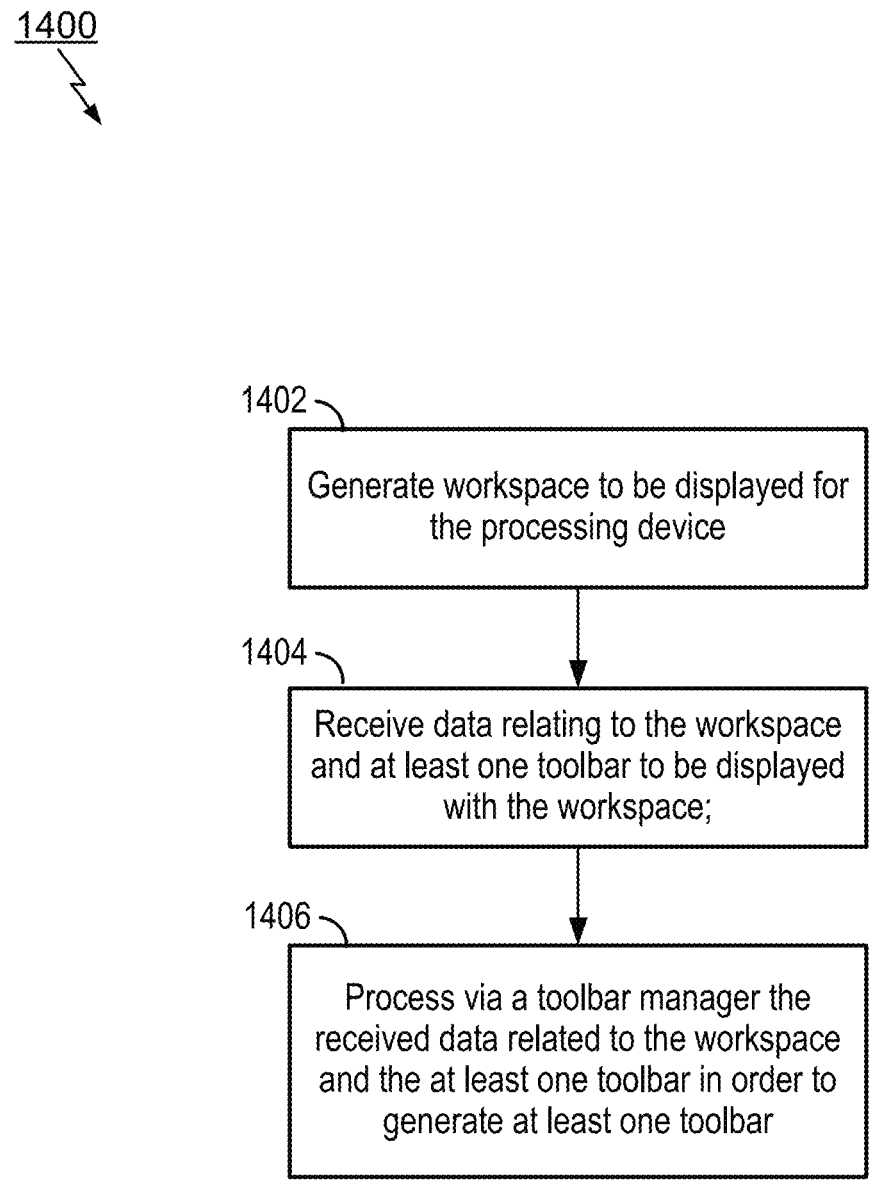
FIG. 14 shows an exemplary method for providing workspace navigation under an illustrative embodiment.

FIG. 14 shows an illustrative method or process 1400 for providing workspace navigation under an illustrative embodiment. Method 1400 includes generating a workspace to be displayed for the processing device as shown at block 1402. The process of block 1402 may be effectuated by a workspace manager/module/circuitry (e.g., 216 in FIG. 2), and may be visually displayed such as the workspace 418 (and associated headers, banners, toolbars 412-416 in an example). Additionally, method 1400 includes receiving data relating to the workspace and at least one toolbar to be displayed with the workspace as shown at block 1404. This process may be implemented by the workspace manager/module/circuitry (e.g., 216) and/or the toolbar manager (e.g., 214), and may include display of the toolbar including action toolbar 410 as shown in FIG. 4, for example.

Furthermore, method 1400 includes processing via a toolbar manager (e.g., 214) the received data related to the workspace and the at least one toolbar in order to generate at least one toolbar as shown in block 1406. The process of block 1406 further includes that the at least one toolbar is configured according to a particular domain and includes one or more areas selectable for expanding the toolbar within the workspace to display information relevant to the particular domain.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing description, it can be seen that various features may be grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the description, with each claim standing on its own as a separate embodiment.

What is claimed is:

1. An apparatus for providing workspace navigation on a processing device, comprising:
   a processor;
   a memory, operatively coupled to the processor;
   a workspace manager configured to generate a workspace for the processing device;
   communications circuitry operatively coupled to the processor, wherein the communications circuitry is configured to receive data relating to the workspace and at least one toolbar via an application programming interface (API); and
   a toolbar manager configured to process the received data related to the workspace and the at least one toolbar from the API via an extension layer of the API, in order to generate at least one toolbar, wherein the at least one toolbar is configured to access data relating to a particular domain of a plurality of domains, each of the plurality of domains comprising different functionality and different customizable action elements specific to each respective domain, while allowing the workspace to remain; and
   wherein the workspace manager is configured to normalize the received data from a plurality of users by modifying the at least one toolbar's functionality and action elements based on a subset of the received data containing authorized metadata for modifying the workspace.

2. The apparatus of claim 1, wherein the toolbar manager configures the toolbar such that at least one area of the toolbar is configured according to the particular domain, wherein the domain includes a particular functionality.

3. The apparatus of claim 2, wherein the toolbar manager is adapted to process the received data to configure the toolbar to include one or more notifications specific to the particular domain.

4. The apparatus of claim 2, wherein the toolbar manager is adapted to process the received data to configure the toolbar to further enable expansion of the toolbar to include view areas to display regarding the particular domain.

5. The apparatus of claim 2, wherein the toolbar manager is adapted to process the received data to configure the toolbar to further enable an expansion of the toolbar during execution of an application and concurrently maintaining a workspace context.

6. The apparatus of claim 2, wherein the toolbar manager is adapted to process the received data to configure the toolbar to further enable an expansion of the toolbar to include view areas to display that relate to a domain different from the particular domain.

7. The apparatus of claim 1, wherein the toolbar manager comprises a core layer and a storage layer operatively coupled to the application programming interface (API) for receiving the data relating to the at least one toolbar.

8. A method for providing workspace navigation on a processing device, comprising:
   generating via a workspace manager a workspace to be displayed for the processing device;
   receiving data via an application programming interface (API) relating to the workspace and at least one toolbar to be displayed with the workspace; and
   processing via a toolbar manager the received data related to the workspace and the at least one toolbar from the API via an extension layer of the API in order to generate at least one toolbar, wherein the at least one toolbar is configured according to a particular domain of a plurality of domains, each of the plurality of domains comprising different functionality and different customizable action elements specific to each respective domain, and includes one or more areas selectable for expanding the toolbar within the workspace to display information relevant to the particular domain; and normalizing, via the workspace manager, the received data from a plurality of users by modifying the at least one toolbar's functionality and action elements based on a subset of the received data containing authorized metadata for modifying the workspace.

9. The method of claim 8, wherein the toolbar manager configures the toolbar such that at least one area of the toolbar is configured according to the particular domain, wherein the domain includes a particular functionality enabling a user to view further information pertinent to the domain.

10. The method of claim 9, wherein the toolbar manager is adapted to process the received data to configure the toolbar to include one or more displayed notifications specific to the particular domain.

11. The method of claim 9, wherein the toolbar manager is adapted to process the received data to configure the toolbar to further enable expansion of the toolbar to include view areas to display regarding the particular domain.

12. The method of claim 9, wherein the toolbar manager is adapted to process the received data to configure the toolbar to further enable an expansion of the toolbar during execution of an application and concurrently maintaining a workspace context.

13. The method of claim 9, wherein the toolbar manager is adapted to process the received data to configure the toolbar to further enable an expansion of the toolbar to include view areas to display that relate to a domain different from the particular domain.

14. The method of claim 8, wherein the toolbar manager comprises a core layer and a storage layer operatively coupled to the application programming interface (API) for receiving the data relating to the at least one toolbar.

15. One or more non-transitory computer readable media containing computer executable instructions for performing a method to modify a workspace on a processing device, the media comprising:

code for generating, with a workspace manager, a workspace to be displayed for the processing device;

code for receiving data via an application programming interface (API) relating to the workspace and at least one toolbar to be displayed with the workspace; and code for processing, with a toolbar manager, the received data related to the workspace and the at least one toolbar from the API via an extension layer of the API in order to generate at least one toolbar, wherein the at least one toolbar is configured according to a particular domain of a plurality of domains specific to each respective domain, each of the plurality of domains comprising different functionality and different customizable action elements, and includes one or more areas selectable for expanding the toolbar within the workspace to display information relevant to the particular domain; and code for normalizing, via the workspace manager, the received data from a plurality of users by modifying the at least one toolbar's functionality and action elements based on a subset of the received data containing authorized metadata for modifying the workspace.

16. The non-transitory computer readable media of claim 15, further comprising code for configuring, via the toolbar manager, the toolbar such that at least one area of the toolbar is configured according to the particular domain, wherein the domain includes a particular functionality enabling a user to view further information pertinent to the domain.

17. The non-transitory computer readable media of claim 16, further comprising code for processing the received data to configure the toolbar to include one or more displayed notifications specific to the particular domain.

18. The non-transitory computer readable media of claim 16, further comprising code for processing the received data to configure the toolbar to further enable expansion of the toolbar to include view areas to display regarding the particular domain.

19. The non-transitory computer readable media of claim 16, further comprising code for processing the received data to configure the toolbar to further enable an expansion of the toolbar during execution of an application and concurrently maintaining a workspace context.

20. The non-transitory computer readable media of claim 16, further comprising code for processing the received data to configure the toolbar to further enable an expansion of the toolbar to include view areas to display that relate to a domain different from the particular domain.

* * * * *